United States Patent [19]
Kortenbach et al.

[11] Patent Number: 5,814,054
[45] Date of Patent: Sep. 29, 1998

[54] AUTOMATIC NEEDLE-PASSER SUTURING INSTRUMENT

[75] Inventors: Juergen Andrew Kortenbach, Miami Springs; Robert Sixto, Jr.; Michael Sean McBrayer, both of Miami, all of Fla.

[73] Assignee: Symbiosis Corporation, Miami, Fla.

[21] Appl. No.: 718,019

[22] Filed: Sep. 23, 1996

[51] Int. Cl.$^6$ .................................................. A61B 17/04
[52] U.S. Cl. .......................... 606/139; 606/144; 606/147; 606/148
[58] Field of Search .................................. 606/139, 144, 606/148, 147

[56] References Cited

U.S. PATENT DOCUMENTS

| | | | |
|---|---|---|---|
| 4,841,888 | 6/1989 | Mills et al. | 112/169 |
| 4,898,157 | 2/1990 | Messroghli et al. | 606/147 |
| 5,037,021 | 8/1991 | Mills et al. | 227/175 |
| 5,080,663 | 1/1992 | Mills et al. | 606/144 |
| 5,330,488 | 7/1994 | Goldrath | 606/148 |
| 5,336,230 | 8/1994 | Leichtling et al. | 606/148 |
| 5,389,103 | 2/1995 | Melzer et al. | 606/144 |
| 5,571,090 | 11/1996 | Sherts | 606/139 |
| 5,630,825 | 5/1997 | De La Torre et al. | 606/139 |
| 5,632,751 | 5/1997 | Piraka | 606/139 |
| 5,645,552 | 7/1997 | Sherts | 606/139 |

OTHER PUBLICATIONS

First clinical Evaluation and Experimental Study of a New Mechanical Suture Device for Endoscopic Hemostasis, J. Escourrou, M.D., et al., Gastrointestinal endoscopy, vol. 36, No. 5, 1990, pp.494–497.

An Endoscopic Sewing Machine, C. Paul Swain et al., Gastrointestinal Endoscopy, vol. 32, No.1, 1986, pp. 36–38.

An Endoscopically Deliverable Tissue–Transfixing Device for Securing Biosensors in the gastrointestinal Tract, C. Paul Swain et al., Gastrointestinal Endoscopy, vol. 40, No. 6, 1994, pp. 730–734.

AutoSuture™ Endostitch™ Instruction Manual, Unites States Surgical Corp, 1994.

*Primary Examiner*—Gary Jackson
*Attorney, Agent, or Firm*—David P. Gordon; David S. Jacobson; Thomas A. Gallagher

[57] ABSTRACT

An automatic suturing instrument generally includes a proximal actuation handle assembly, a flexible tubular member, a control wire, and an end effector assembly. The control wire extends through the tubular member and the end effector-assembly is coupled to the distal end of each of the tubular member and the control wire, while the handle is coupled to the proximal end of each of the tubular member and the control wire. Actuation of the handle moves the control wire relative to the tubular member and thereby moves the end effector assembly from an open to a closed position. The end effector assembly generally includes two end effectors, a needle engaged by one of the end effectors (but which can be engaged by either end effector alternately), and a suture material. The end effector assembly further includes a needle passing mechanism that automatically alternates which end effector engages the needle each time the end effectors are moved into a closed position.

22 Claims, 7 Drawing Sheets

AUTOMATIC NEEDLE-PASSER SUTURING INSTRUMENT

BACKGROUND OF THE INVENTION

1. Field of the Invention

This invention relates broadly to surgical suturing instruments. More particularly, this invention relates to laparoscopic automatic needle-passer suturing instruments.

2. State of the Art

Laparoscopic suturing instruments are used for placing stitches in soft tissue. Typically, a small incision is formed in the abdominal cavity of a patient via the use of a trocar which is used to puncture the skin and fascia of the patient. The laparoscopic suturing instrument can then be passed through the trocar tube which is left in place in the incision.

A prior art laparoscopic suturing instrument is sold under the AutoSuture EndoStitch trademark by United States Surgical Corp., Norwalk, Conn. The EndoStitch includes a proximal handle, a rigid tubular member and a control wire extending therethrough, a stitching end effector assembly, a toggling switching lever for engaging and disengaging a needle in the end effector assembly, arrow alignment indicia for aligning the toggle switch, and a needle reloading button set. The control wire extends through the tubular member and the end effector assembly is coupled to the distal end of each of the tubular member and the control wire, while the handle is coupled to the proximal end of each of the tubular member and the control wire. The end effector assembly generally includes two stitching end effectors and a needle. The end effectors are rotatable relative to each other. The needle is engaged in one of the end effectors, but can be engaged by either end effector, and is provided with a suture material. Actuation of the handle moves the control wire relative to the tubular member and thereby moves the end effectors from an open to a closed position.

The practitioner actuates the handle to open the end effector assembly and carefully guides the end effectors around the tissue to be sutured. When the end effectors are in the correct position, the practitioner manipulates the handle to close the end effectors on the tissue to be sutured. As the end effectors close, the needle passes into and through the tissue and contacts the second end effector on the other side of the tissue. The practitioner is then required to toggle the switching lever to lock the needle in one end effector and to unlock the needle from the other end effector. The practitioner then operates the handle to open the end effectors and transfer the needle from one side of the tissue to the other side of the tissue. Consequently, the suture is pulled through the tissue. The process is repeated for as many sutures as the practitioner desires. The suture is then tied and cut by another instrument and the instruments are removed from the surgical site.

As suggested above, the AutoSuture™ EndoStitch instrument requires a complex operation to pass the needle from one end effector to the other. Failure to toggle the switch will result in the needle not being passed from one end effector to the other. Furthermore, care must be made to not toggle the switch during a suturing procedure, as the needle may be dislodged from the instrument or the needle may be prevented from engaging with the other end effector. Another shortcoming of the AutoSuture Endostitch instrument is that two-handed operation is required in unloading the needle from the AutoSuture™ EndoStitch instrument. One hand must align the toggle levers with arrow indicia on the housing of the instrument while simultaneously squeezing the handles. The other hand must simultaneously depress reloading buttons on both the front and back of the instrument. This operation will cause the reloading buttons to advance position. Then the handle can be released and the needle can be removed. Moreover, the mechanism of the Autosuture™ device incorporates a complex array of wires running through the entire length of the rigid tubular member.

The suturing process poses several challenges to the design and manufacture of a surgical suturing instrument. Presently, the manner in which the needle is passed from one end effector to the other and pulled through the tissue, and the manner in which the needle is unloaded from and reloaded in the instrument are inefficient and cumbersome with the instruments of the prior art. In addition, the complex array of wires utilized in the mechanism of the prior art instruments is not conducive to an instrument having a flexible design.

SUMMARY OF THE INVENTION

It is therefore an object of the invention to provide a suturing instrument which is easy to use by the practitioner.

It is also an object of the invention to provide a suturing instrument which is flexible.

It is a further object of the invention to provide a suturing instrument which automatically switches engagement of a needle between two end effectors.

It is another object of the invention to provide a suturing instrument which assists in passing a needle through tissue at the suturing site.

It is yet another object of the invention to provide a suturing instrument having an easily replaceable needle.

In accord with these objects which will be discussed in detail below, an automatic endoscopic suturing instrument is provided. The instrument generally includes a proximal-actuation handle assembly, a flexible tubular member, a control wire, and an end effector assembly. The control wire extends through the tubular member and the end effector assembly is coupled to the distal end of each of the tubular member and the control wire, while the handle is coupled to the proximal end of each of the tubular member and the control wire. Actuation of the handle moves the control wire relative to the tubular member and thereby moves the end effector assembly from an open to a closed position. The end effector assembly generally includes two end effectors, a needle engaged by one of the end effectors at a time (but which can be engaged by either end effector alternately), and a suture material. The end effector assembly further includes a needle passing mechanism that automatically alternates which end effector engages the needle each time the end effectors are moved into a closed position, and two blades which extend through the end effectors which may, if desired, bias the end effectors toward an open position. In addition, the two blades also cooperate with the needle passing mechanism to lock the needle in one of the end effectors. When a blade is locking the needle that blade extends out of the distal end of the end effector holding the needle. The needle may be released from that end effector by simply tapping the distal end of the end effector on a hard surface to depress the blade extending out of the distal end of the end effector or alternatively pressing the blade with a human finger. A new needle with suture may then be inserted in and engaged by an end effector.

With the above embodiment it will be appreciated that the automatic suturing instrument of the invention is easily operable, requiring no additional effort to alternate engagement of the needle by the end effectors beyond actuating the handle to open and close the end effectors. In addition, the manner of removing a needle and inserting a new needle with suture into the end effector is greatly simplified.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
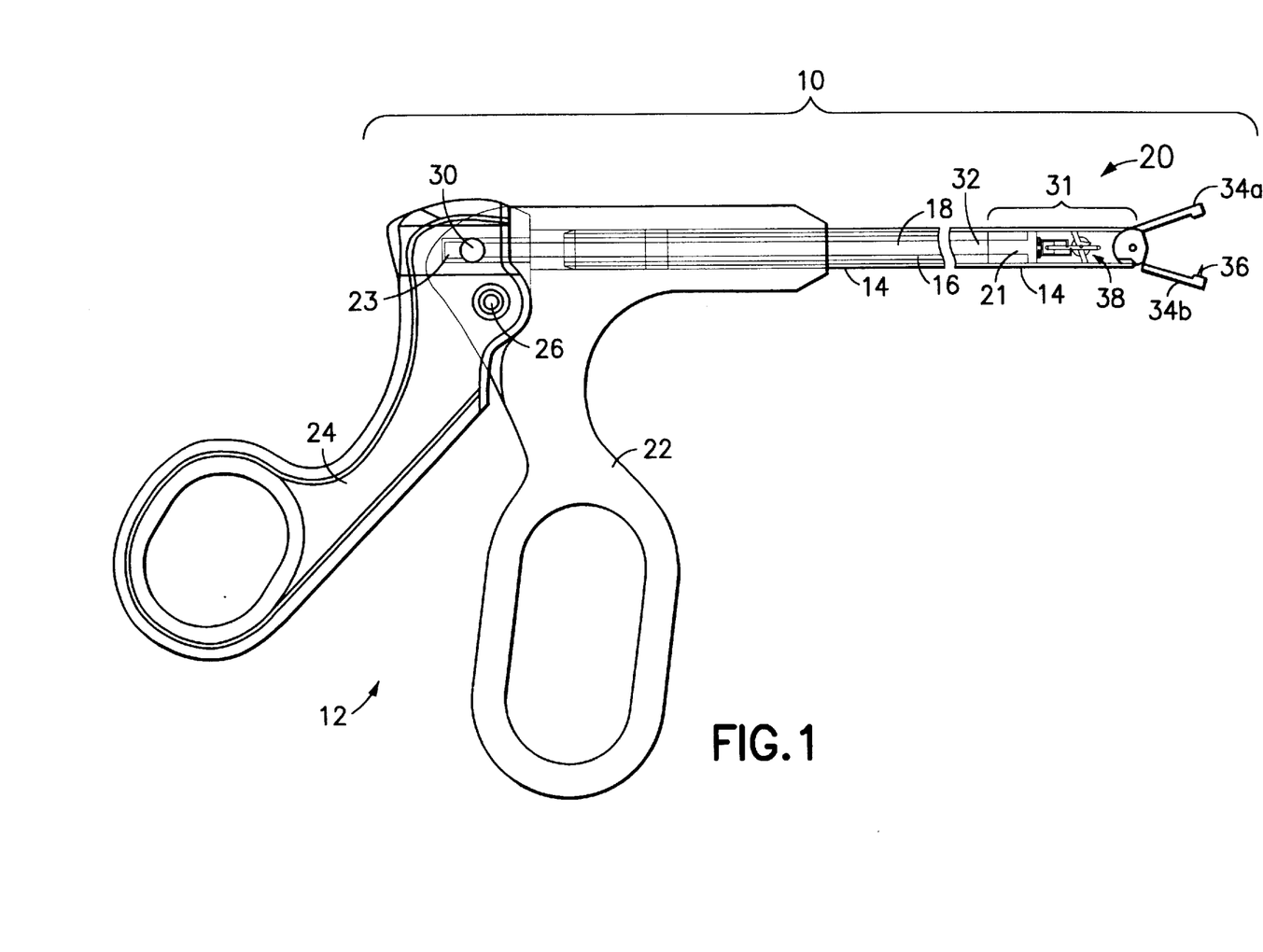
FIG. 1 is a broken transparent partial side elevation view of an automatic suturing instrument according to the invention.

Turning now to FIG. 1, an automatic endoscopic suturing instrument 10 is shown. The suturing instrument includes a proximal actuation handle assembly 12, a tubular member 14 having a lumen 16, a control wire 18 (or push rod) extending through the lumen, and an end effector assembly 20. The proximal actuation handle assembly 12 includes a fixed handle portion 22 and a lever 24 pivotally coupled to the fixed handle portion by a pivot pin 26. The tubular member is preferably a flexible coil, but may also be a rigid tube. The proximal end of the tubular member 14 is fixedly coupled to the handle portion 22. The lumen 16 of the tubular member 14 is sized to permit the control wire 18 to freely move axially but preferably to allow only a small amount of radial movement. The distal end of the tubular member is provided with a clevis 28. The control wire 18 is coupled at its proximal end 23 to the lever 24 by an axle 30 in a known manner and is provided at its distal end 32 with a coupling structure 21. As will be described in more detail below, the coupling structure 21 includes a mounting block 35, a post 37, and a bracket 39 which support various parts of the end effector assembly 20.

Figure 2:
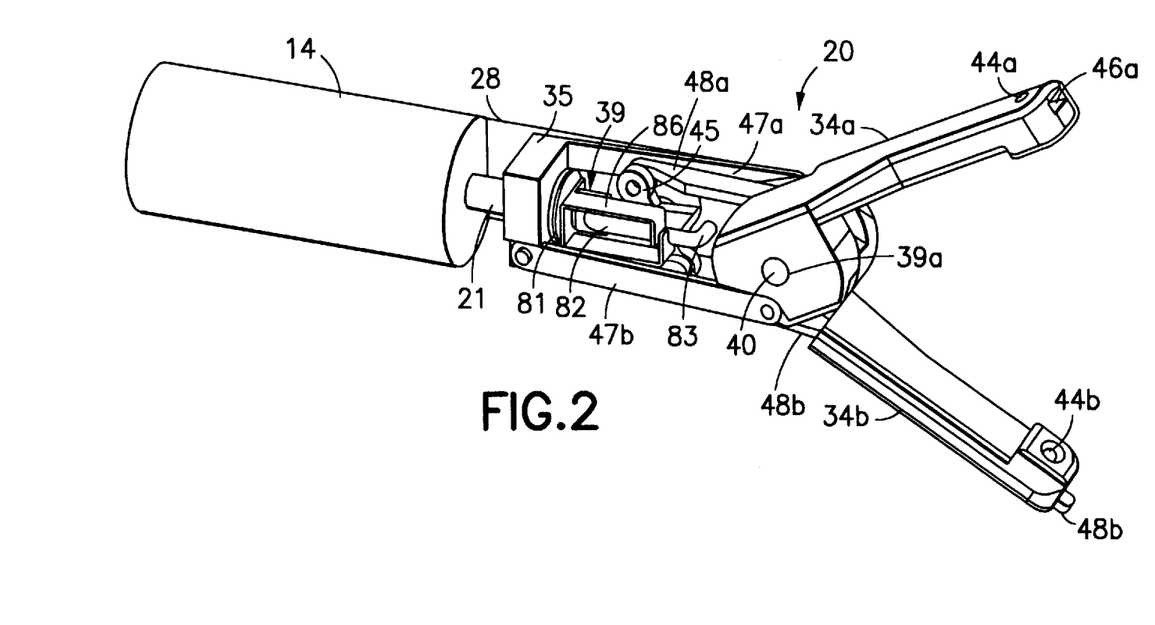
FIG. 2 is an enlarged broken cutaway perspective view of the distal end of the suturing instrument of FIG. 1.
Figure 3:
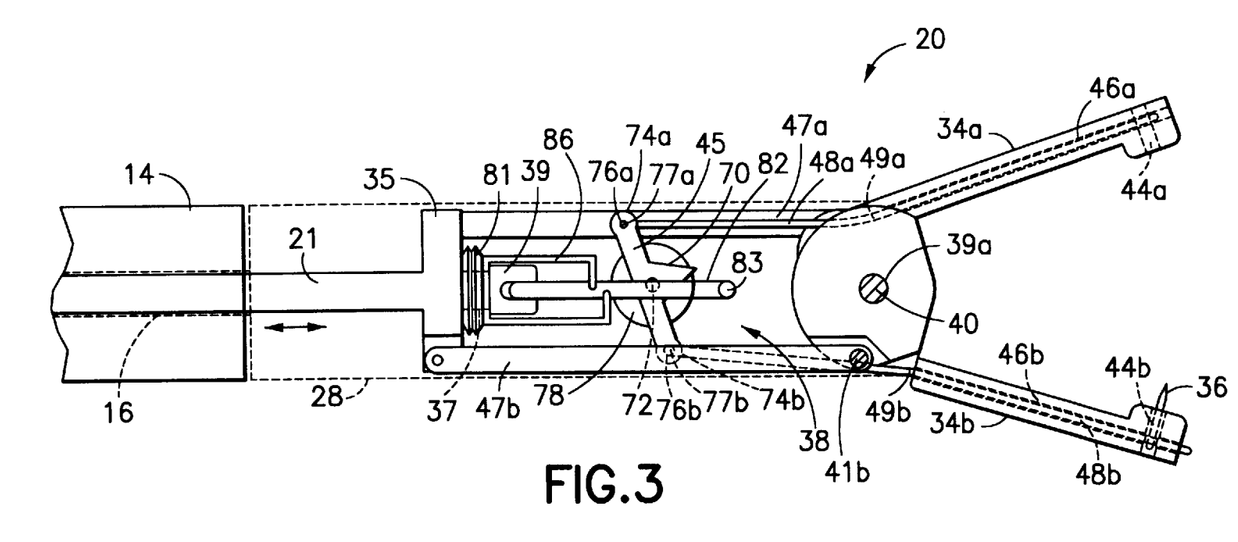
FIG. 3 is an enlarged broken side view schematic of the distal end of the suturing instrument of FIG. 1.
Figure 4:
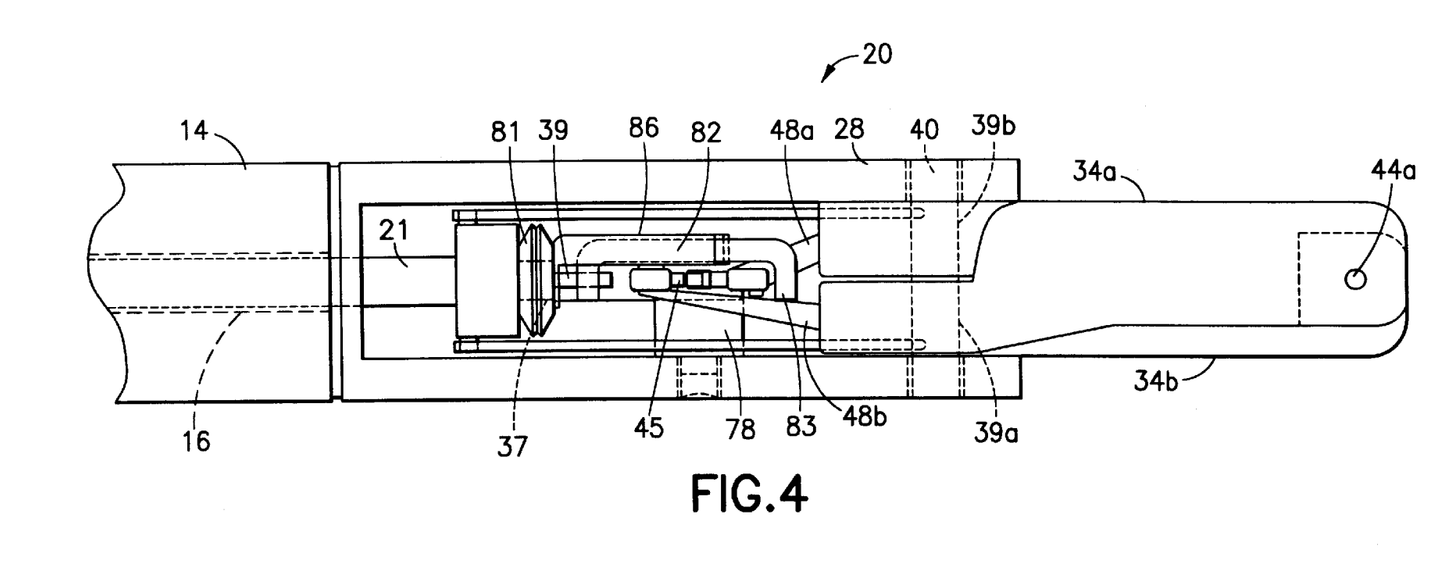
FIG. 4 is an enlarged broken bottom view schematic of the distal end of the suturing instrument of FIG. 1.

Turning to FIGS. 2, 3, and 4, the end effector assembly 20 generally includes two end effectors 34a, 34b, an elongate needle 36 (shown only with respect to FIG. 3) locked in one of the end effectors 34b but lockable by either, and a needle transfer assembly 38. The two end effectors 34a, 34b each have a mounting bore 39a, 39b and are rotatably mounted at the mounting bore on an axle 40 between the arms of the clevis 28. Each end effector 34a, 34b also includes a proximal tang 41a, 41b which is coupled by a link 47a, 47b to diagonally opposed sides of the mounting block 35 of the coupling structure 21. Each end effector 34a, 34b further includes a distal needle receiving hole 44a, 44b, and a longitudinal blade receiving channel 46a, 46b which intersects the needle receiving hole and preferably extends through the distal end of the end effectors. When the end effectors are in a closed position, the needle receiving holes are mutually aligned.

Blades 48a, 48b, preferably resilient and made of spring steel or Nitinol, extend through the blade receiving channel 46a, 46b. Each blade 48a, 48b is preferably provided with a bend 49a, 49b located where the blade enters the blade receiving channel and angled away from the longitudinal axis of the tubular member 14. If desired, the blades may be of a strength and angled such that the end effectors are biased toward an open position.

Figure 5:
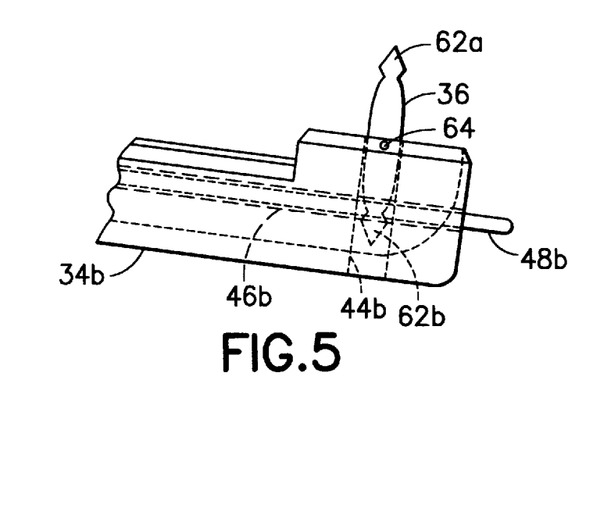
FIG. 5 is an enlarged broken side elevational view of the distal end of an end effector of the suturing instrument of FIG. 1.
Figure 6A:
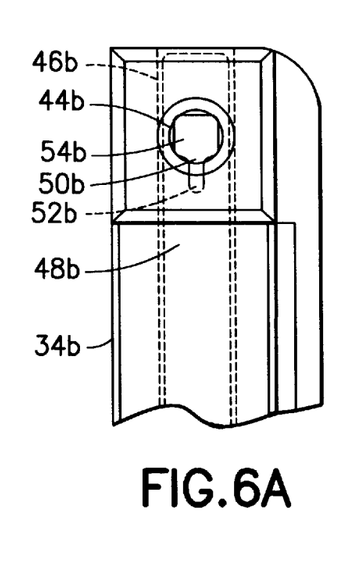
FIGS. 6A and 6B are enlarged broken partial top views of the distal end of an end effector of the suturing instrument of FIG. 1.
Figure 6B:
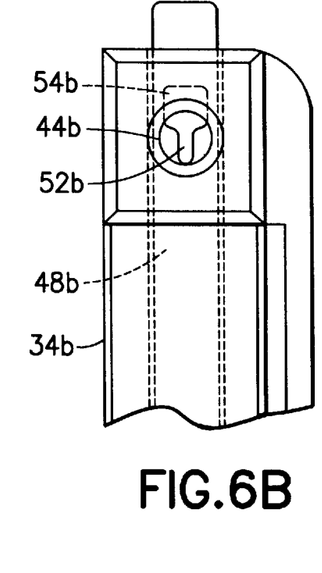

Referring to FIG. 5 (shown with the needle 36 and with respect to one end effector 34b) and FIGS. 6A and 6B (shown without the needle 36 and with respect to one end effector 34b), the distal end of each blade 48b defines a keyhole 50b for receiving the needle 36. The keyhole 50b has a narrow lock portion 52b and a wider release portion 54b. A circumferential groove 62a, 62b is provided at each end of the needle 36 for engagement by the blade at the lock 52b, and a central eye 64 is provided for receiving a suture material. When the blade 48b is situated in the channel 46b such that the release 54b of the keyhole 50b intersects the needle receiving hole 44b, the needle is in a needle-release position and the needle may freely enter or exit the needle receiving hole 44b. When the needle 36 is inserted in the needle receiving hole 44b, distal movement of the blade 48b moves the locking portion 52b of the keyhole into engagement with the circumferential groove 62b of the needle such that the blade moves into a needle-lock position. When the blade 48b is in the needle-lock position, the distal end of the blade preferably extends through the distal end of the channel 46b.

Referring back to FIGS. 2, 3, and 4, a rocking lever 45 is provided which is coupled by a pivot 72 to one arm of the clevis 28 with a cylindrical spacer 78. The lever 45 includes a central tooth 70 which extends distally and first and second arms 74a, 74b on either side of the pivot 72. The first and second arms are each provided with a coupling bore 76a, 76b which is rotatably coupled to a respective tang 77a, 77b at the proximal end of a respective one of the blades 48a, 48b. A rigid switch pin 82, preferably having an L-shaped distal end 83, is fixedly coupled to the bracket 39 of the mounting rod 21. A resilient washer 81, or a coil spring, is situated on the mounting rod 21, interposed between the bracket 39 and the mounting block 35. A spring 86 is positioned between the washer 81 and the bracket 39. The spring 86 biases the switch pin 82 to a center position parallel to the longitudinal axis of the tubular member 14.

It will be appreciated that movement of the lever 24 relative to the handle portion 22 moves the control wire 18 relative to the tubular member 14, and thereby opens and closes the end effectors 34a, 34b. It will be further appreciated that as the control wire 18 is moved proximally relative to the tubular member, the switch pin 86 is moved proximally from a distal position. The distal end 83 of the switch pin 82 will ride on one side of the tooth 70, engage the first arm, and rotate the lever such that the first and second arms and the two blades are moved into reciprocal positions. The resilient washer 81 is provided with enough resiliency to permit the switch pin to rotate the lever after the end effectors have closed. When the switch pin is moved distally and again proximally it will ride down the other side of the tooth and thereby again cause reciprocal movement of the arms and, likewise, the blades. Each reciprocal movement of the blades will alternate which blade is in a needle-lock position and which blade is in a needle-release position. If the blades are designed to bias the end effectors into an open position, the blades will thereby assist in pulling the needle through tissue. Regardless, one actuation cycle of the proximal actuation handle assembly will close the end effectors on an area of tissue, transfer the needle from one end effector to the other, and open the end effectors so that the suture material is pulled through the tissue. Multiple stitches may be made by moving the distal end of the end effectors further along the tissue and repeating the process.

It will be further appreciated that the needle may be manually released by tapping on a hard surface the distal end of the end effector in which the needle is engaged, thereby forcing proximally the portion of the blade which extends through the distal end of the end effector and unlocking the needle. The needle will then be disengaged from the blade and the needle can be extricated. If the needle cannot be freely extricated from the needle receiving hole 44a, 44b (for example, if there is no suture to pull on or if a piece of tissue becomes lodged with the needle), a small pin (not shown) may be placed through the exterior side of the needle receiving hole and the needle may be pushed out of the interior side of the needle receiving hole.

It also will be appreciated that by locating substantially all of the needle passing mechanism at the end effector assembly and by having only a control wire extending through the tubular member, a flexible automatic needle passing suturing instrument can be provided. This is in contrast to the instruments of the prior art which have their operating mechanisms in both the proximal and distal portions of the instruments.

Figure 7:
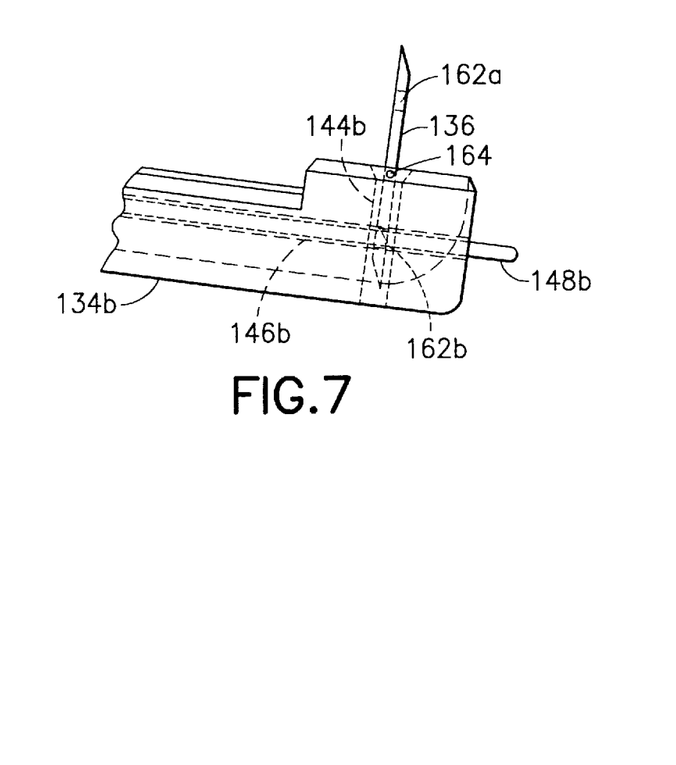
FIG. 7 is a view similar to FIG. 5 of a second embodiment of a suturing instrument according to the invention.
Figure 8A:
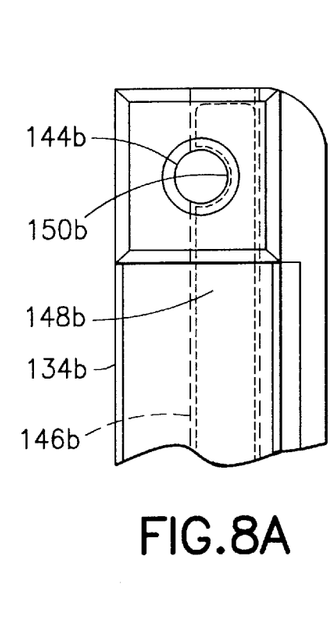
FIGS. 8A and 8B are views similar to FIGS. 6A and 6B of the second embodiment of a suturing instrument according to the invention.
Figure 8B:
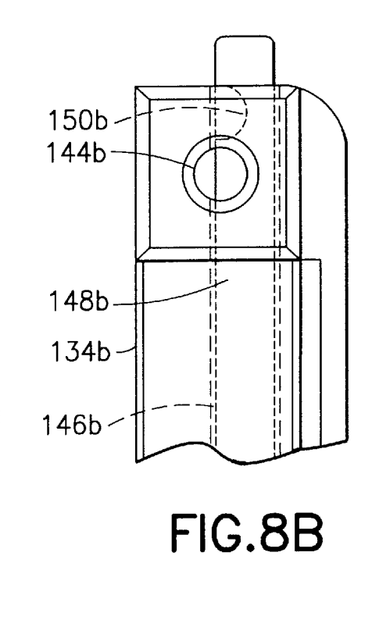

Turning now to FIGS. 7, 8A and 8B, a second embodiment, substantially similar to the first embodiment (with similar parts having numbers incremented by 100), is shown. Each of two end effectors (shown without the needle and with respect to one end effector 134b) includes a longitudinal blade channel 146b, laterally offset from the longitudinal axis of the end effector, and a distal needle receiving hole 144b such that when the end effectors 134a, 134b are in a closed position the needle receiving holes 144a, 144b are mutually aligned. Each of two blades 148b has a notched cutout 150b and extends through the channel 146b of each end effector. When a blade is positioned within the channel 146b such that the notched cutout 150b intersects the needle receiving hole 144b, that blade is in a needle-release position. If that blade is moved proximally the blade will partly obstruct the needle receiving hole and be in a needle-lock position. A needle 136 has a notch 162a, 162b at each of two ends and a central eye 164 for receiving a suture material. When the needle 136 is received within the needle receiving hole and the blade 148b is moved distally extending into the notch 162a, 162b, the blade engages the needle. When the blade is moved proximally within the channel and the notched cutout 150b again intersects the needle receiving hole 144b and the needle is released.

Figure 9:
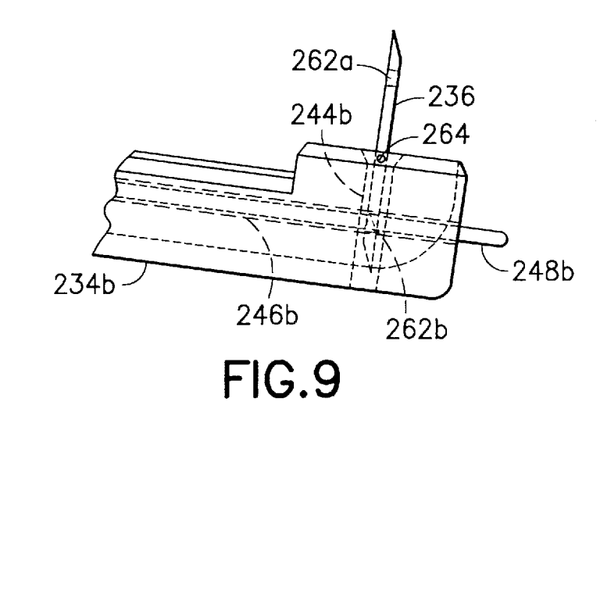
FIG. 9 is a view similar to FIG. 5 of a third embodiment of a suturing instrument according to the invention.
Figure 10A:
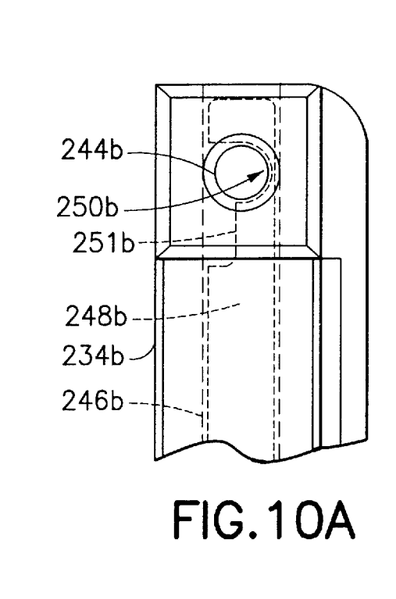
FIGS. 10A and 10B are views similar to FIGS. 6A and 6B of the third embodiment of a suturing instrument according to the invention.
Figure 10B:
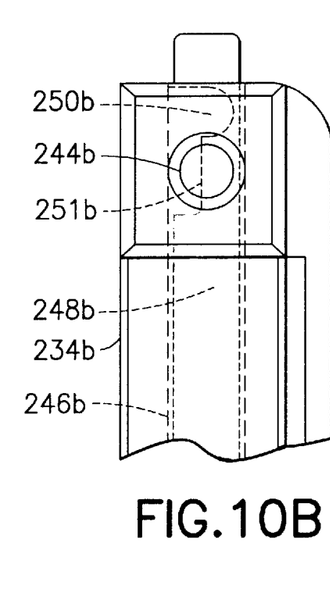

Turning now to FIGS. 9, 10A and 10B, a third embodiment, substantially similar to the first embodiment (with similar parts having numbers incremented by 200), is shown. Each of two end effectors (shown without the needle and with respect to one end effector 234b) includes a central longitudinal blade channel 246b, symmetrical along the longitudinal axis of the end effector, and a distal needle receiving hole 244b such that when the end effectors are in a closed position the needle receiving holes of each end effectors are mutually aligned. Each of two blades 248b includes two notched cutouts 250b, 251b wherein one notched cutout 250b is deep and the other notched cutout 251b is shallow. When a blade is positioned within the channel 246b such that the deeper notched cutout 250b intersects the needle receiving hole 244b, that blade is in a needle-release position. When the blade is positioned within the channel 246b such that the shallow notched cutout 251b is aligned with the needle receiving hole 244b, the passageway of the needle receiving hole is obstructed. A needle 236 has a notch 262a, 262b at each of two ends and a central eye 264 for receiving a suture material. When the needle 236 is received within the needle receiving hole and the blade 248b is moved distally, the blade lateral of the shallow notch 251b extends into the notch 262b and engages the needle. The needle is released when the blade is moved proximally within the channel and the deeper notched cutout 250b again intersects the needle receiving hole 244b.

There have been described and illustrated herein several embodiments of a endoscopic suturing instrument. While particular embodiments of the invention have been described, it is not intended that the invention be limited thereto, as it is intended that the invention be as broad in scope as the art will allow and that the specification be read likewise. Thus, while one particular proximal actuation handle assembly has been disclosed, it will be appreciated that other proximal actuation handle assemblies could likewise be used for the instrument. For example, and not by way of limitation, a handle rotatable relative to the end effectors could be used as disclosed in co-owned U.S. Ser. No. 08/284,793 which is hereby incorporated by reference herein. Furthermore, while it has been disclosed that the instrument has a preferably flexible tubular member (e.g., a coil) and control wire, it will be appreciated that using methods known in the art an instrument having a rigid tubular member and/or a push rod could likewise be designed. In addition, while particular types of couplings have been disclosed for the various parts of the instrument, it will be understood that other methods known in the art for coupling the parts can be used. Also, while a notched or grooved needle is preferred, it will be recognized that other configurations of the needle which provide means for engagement can also be used. In addition, other blade keyhole or notch configurations can also be used. Furthermore, while the switch pin is disclosed as having an L-shaped distal end, it will be appreciated that another bend in the pin, for example a U-shape at the distal end, can also be used. Moreover, while the blades have been disclosed as potentially having the ability to bias the end effectors into an open position and thereby assist in pulling the needle through the tissue, it will also be appreciated that in the alternative the handle could be biased with a spring or other means such that the end effectors are biased into an open position. It will therefore be appreciated by those skilled in the art that yet other modifications could be made to the provided invention without deviating from its spirit and scope as so claimed.

We claim:

1. A suturing instrument for use in conjunction with a needle, comprising:

a) a flexible tubular member having a distal end;

b) an actuation means extending through said tubular member, said actuation means having a handle means and one of a control wire and a push rod, said handle means being coupled to said one of said control wire and said push rod for moving said one of said control wire and said push rod relative to said tubular member;

c) first and second stitching end effectors coupled to said tubular member, at least one of said first end second stitching end effectors adapted to move relative to the other, said first and second stitching end effectors having a releasable needle gripping means for releasably gripping the needle; and d) an automatic needle switching means coupled to said needle gripping means and activated by said actuation means, wherein said first and second stitching end effectors are adapted to be movable from a first position to a second position to a third position to a fourth position and back to said first position, and in said first position said first and second stitching end effectors are in an open position and said first end effector is adapted to grip the needle, in said second position said first and second stitching end effectors are in a closed position and said first end effector is adapted to automatically release the needle and said second end effector is adapted to automatically grip the needle, in said third position said first and second stitching end effectors are in said open position and said second end effector is adapted to grip the needle, and in said fourth position said first and second stitching end effectors are in said closed position and said first end effector is adapted to automatically grip the needle and said second end effector is adapted to automatically release the needle.

2. A suturing instrument a according to claim 1, wherein: said tubular member is a coil.

3. A suturing instrument for use in conjunction with a needle, comprising:

a) a tubular member having a distal end;

b) an actuation means extending through said tubular member;

c) first and second stitching end effectors coupled to said tubular member, said first end second stitching end effectors adapted to move from an open position to a closed position, said first and second stitching end effectors defining first and second longitudinal channels, respectively, and further defining first and second distal needle receiving means, respectively, for receiving the needle;

d) first and second blades received in said first and second channels, respectively, said first and second blades defining first and second needle gripping means for aligning with said first and second needle receiving means and gripping the needle; and e) an automatic needle switching means coupled to said first and second blades and activated by said actuation means, said needle switching means for reciprocally moving said first and second blades axially within said first and second channels, wherein when the needle is gripped in one of said first and second needle gripping means, actuation of said actuation means moves said first and second end effectors into said closed position and further activate said automatic needle switching means to move said first and second blades relative to each other and grip the needle in the other of said first and second needle gripping means.

4. A suturing instrument according to claim 3, wherein: said actuation means comprises a handle means and one of a control wire and a push rod, said handle means being coupled to said one of said control wire and said push rod for moving said one of said control wire and said push rod relative to said tubular member.

5. A suturing instrument according to claim 4, wherein: said tubular member is flexible.

6. A suturing instrument according to claim 5, wherein: said tubular member is a coil.

7. A suturing instrument according to claim 3, further comprising:

f) a needle received in one of said first and second needle receiving means and gripped by one of said first and second needle gripping means.

8. A suturing instrument according to claim 3, wherein: said first and second blades are biased such that said first and second end effectors are biased in said open position.

9. A suturing instrument according to claim 3, wherein: said first and second needle gripping means are keyholes defined by said first and second blades.

10. A suturing instrument according to claim 3, wherein: said first end effector is provided with a distal end and when the needle is gripped in said first needle gripping means, said first blade extends beyond said distal end.

11. A suturing instrument according to claim 4, wherein: said one of said control wire and said push rod has a distal end and said needle switching means includes i) a switch pin coupled to said distal end of said one of said control wire and said push rod, and ii) a lever defining a distally-extending tooth and two arms, said lever pivotally coupled to said distal end of said tubular member and said two arms pivotally coupled to said first and second blades, respectively.

12. A suturing instrument according to claim 11, wherein: said needle switching means further includes iii) a spring biasing said switch pin parallel to said tubular member.

13. A suturing instrument, comprising:

a) a needle having a first and second sharp ends;

b) a tubular member having a distal end;

c) an actuation means extending through said tubular member, said actuation means having a handle means and one of a control wire and a push rod, said handle means being coupled to said one of said control wire and said push rod for moving said one of said control wire and said push rod relative to said tubular member;

d) first and second stitching end effectors coupled to said tubular member, at least one of said first end second stitching end effectors adapted to move relative to the other, said first and second stitching end effectors having a releasable needle gripping means for releasably gripping said needle; and e) an automatic needle switching means coupled to said needle gripping means and activated by said actuation means, wherein said first and second stitching end effectors are adapted to be movable from a first position to a second position to a third position to a fourth position and back to said first position, and in said first position said first and second stitching end effectors are in an open position and said first end effector is adapted to grip said needle, in said second position said first and second stitching end effectors are in a closed position and said first end effector is adapted to automatically release said needle and said second end effector is adapted to automatically grip said needle, in said third position said first and second stitching end effectors are in said open position and said second end effector is adapted to grip said needle, and in said fourth position said first and second stitching end effectors are in said closed position and said first end effector is adapted to automatically grip the needle and said second end effector is adapted to automatically release the needle.

14. A suturing instrument for use in conjunction with a needle, comprising:
   a) a tubular member having a distal end;
   b) an actuation means extending through said tubular member, said actuation means having a handle means and one of a control wire and a push rod, said handle means being coupled to said one of said control wire and said push rod for moving said one of said control wire and said push rod relative to said tubular member;
   c) first and second stitching end effectors coupled to said tubular member, at least one of said first end second stitching end effectors adapted to move relative to the other, said first and second stitching end effectors having a releasable needle gripping means for releasably gripping said needle, said needle gripping means having first and second sliding members each defining a keyhole, and said first stitching end effector defining a first channel in which said first sliding member is received and said second end effector defining a second channel in which said second sliding member is received; and
   d) an automatic needle switching means coupled to said needle gripping means and activated by said actuation means,
   wherein said first and second stitching end effectors are adapted to be movable from a first position to a second position to a third position to a fourth position and back to said first position, and in said first position said first and second stitching end effectors are in an open position and said first end effector is adapted to grip said needle, in said second position said first and second stitching end effectors are in a closed position and said first end effector is adapted to automatically release said needle and said second end effector is adapted to automatically grip said needle, in said third position said first and second stitching end effectors are in said open position and said second end effector is adapted to grip said needle, and in said fourth position said first and second stitching end effectors are in said closed position and said first end effector is adapted to automatically grip the needle and said second end effector is adapted to automatically release the needle.

15. A suturing instrument for use in conjunction with a needle, comprising:
   a) a tubular member having a distal end;
   b) an actuation means extending through said tubular member, said actuation means having a handle means and one of a control wire and a push rod, said handle means being coupled to said one of said control wire and said push rod for moving said one of said control wire and said push rod relative to said tubular member;
   c) first and second stitching end effectors coupled to said tubular member, at least one of said first end second stitching end effectors adapted to move relative to the other, said first and second stitching end effectors having a releasable needle gripping means for releasably gripping said needle, said needle gripping means having first and second sliding members each defining at least one notch, and said first stitching end effector defining a first channel in which said first sliding member is received and said second end effector defining a second channel in which said second sliding member is received; and
   d) an automatic needle switching means coupled to said needle gripping means and activated by said actuation means,
   wherein said first and second stitching end effectors are adapted to be movable from a first position to a second position to a third position to a fourth position and back to said first position, and in said first position said first and second stitching end effectors are in an open position and said first end effector is adapted to grip said needle, in said second position said first and second stitching end effectors are in a closed position and said first end effector is adapted to automatically release said needle and said second end effector is adapted to automatically grip said needle, in said third position said first and second stitching end effectors are in said open position and said second end effector is adapted to grip said needle, and in said fourth position said first and second stitching end effectors are in said closed position and said first end effector is adapted to automatically grip the needle and said second end effector is adapted to automatically release the needle.

16. A suturing instrument according to claim 15, wherein:
   when said first and second end effectors are in said first position, said first sliding member extends beyond said first channel.

17. The suturing instrument according to claim 15, wherein:
   said one of said control wire and said push rod has a distal end and said needle switching means includes
      i) a switch pin coupled to said distal end of said one of said control wire and said push rod, and
      ii) a lever defining a distally-extending tooth and two arms, said lever pivotally coupled to said distal end of said tubular member and said two arms pivotally coupled to said first and second sliding members, respectively.

18. A suturing instrument for use in conjunction with a needle, comprising:
   a) a tubular member having a distal end;
   b) an actuation means extending through said tubular member, said actuation means having a handle means and one of a control wire and a push rod, said handle means being coupled to said one of said control wire and said push rod for moving said one of said control wire and said push rod relative to said tubular member;
   c) first and second stitching end effectors coupled to said tubular member, at least one of said first end second stitching end effectors adapted to move relative to the other, said first and second stitching end effectors having a releasable needle gripping means for releasably gripping said needle, said needle gripping means having first and second resilient sliding members, and said first stitching end effector defining a first channel in which said first sliding member is received and said second end effector defining a second channel in which said second sliding member is received; and
   d) an automatic needle switching means coupled to said needle gripping means and activated by said actuation means,
   wherein said first and second stitching end effectors are adapted to be movable from a first position to a second position to a third position to a fourth position and back to said first position, and in said first position said first and second stitching end effectors are in an open position and said first end effector is adapted to grip said needle, in said second position said first and second stitching end effectors are in a closed position and said first end effector is adapted to automatically release said needle and said second end effector is adapted to automatically grip said needle, in said third position said first and second stitching end effectors are in said open position and said second end effector is adapted to grip said needle, and in said fourth position said first and second stitching end effectors are in said closed position and said first end effector is adapted to automatically grip the needle and said second end effector is adapted to automatically release the needle.

19. A suturing instrument according to claim 18, wherein:
said first and second sliding members are provided with a bend such that said first and second end effectors are biased into said open position.

20. A suturing instrument for use in conjunction with a needle, comprising:
a) a tubular member having a distal end;
b) an actuation means extending through said tubular member, said actuation means having a handle means and one of a control wire and a push rod, said handle means being coupled to said one of said control wire and said push rod for moving said one of said control wire and said push rod relative to said tubular member, said one of said control wire and said push rod having a distal end;
c) first and second stitching end effectors coupled to said tubular member, at least one of said first end second stitching end effectors adapted to move relative to the other, said first and second stitching end effectors having a releasable needle gripping means for releasably gripping said needle, said needle gripping means having first and second sliding members, and said first stitching end effector defining a first channel in which said first sliding member is received and said second end effector defining a second channel in which said second sliding member is received; and
d) an automatic needle switching means coupled to said needle gripping means and activated by said actuation means, said needle switching means including,
    i) a switch pin coupled to said distal end of said one of said control wire and said push rod, and
    ii) a lever defining a distally-extending tooth and two arms, said lever pivotally coupled to said distal end of said tubular member and said two arms pivotally coupled to said first and second sliding members, respectively,
wherein said first and second stitching end effectors are adapted to be movable from a first position to a second position to a third position to a fourth position and back to said first position, and in said first position said first and second stitching end effectors are in an open position and said first end effector is adapted to grip said needle, in said second position said first and second stitching end effectors are in a closed position and said first end effector is adapted to automatically release said needle and said second end effector is adapted to automatically grip said needle, in said third position said first and second stitching end effectors are in said open position and said second end effector is adapted to grip said needle, and in said fourth position said first and second stitching end effectors are in said closed position and said first end effector is adapted to automatically grip the needle and said second end effector is adapted to automatically release the needle.

21. The suturing instrument according to claim 20, wherein:
said needle switching means further includes
    iii) a spring biasing said switch pin parallel to said tubular member.

22. A suturing instrument according to claim 21, further comprising:
e) a first link and a second link, said first link adapted to couple said first end effector to said one of said control wire and said push rod and said second link adapted to couple said second end effector to said one of said control wire and said push rod.

* * * * *